United States Patent [19]

Gehring et al.

[11] Patent Number: 4,740,231
[45] Date of Patent: Apr. 26, 1988

[54] 1-ARYL-5-ALKOXIMINOALKYLAMINO-PYRAZOLES, COMPOSITION CONTAINING THEM, HERBICIDAL AND PLANT-GROWTH REGULATING METHOD OF USING THEM, AND INTERMEDIATES IN THE PREPARATION OF THEM

[75] Inventors: Reinhold Gehring, Wuppertal; Otto Schallner, Monheim; Jörg Stetter, Wuppertal; Hans-Joachim Santel, Leverkusen; Robert R. Schmidt; Klaus Lürssen, both of Bergisch-Gladbach, all of Fed. Rep. of Germany

[73] Assignee: Bayer Aktiengesellschaft, Leverkusen, Fed. Rep. of Germany

[21] Appl. No.: 866,510

[22] Filed: May 22, 1986

[30] Foreign Application Priority Data

Jun. 7, 1985 [DE] Fed. Rep. of Germany ....... 3520331

[51] Int. Cl.$^4$ .................. A01N 43/56; C07D 231/38; C07D 401/14
[52] U.S. Cl. ........................................ 71/92; 71/90; 544/2; 544/5; 544/7; 544/8; 544/55; 544/56; 544/60; 544/63; 544/65; 544/66; 544/67; 544/96; 544/98; 544/124; 544/131; 544/140; 544/182; 544/198; 544/207; 544/212; 544/217; 544/218; 544/219; 544/238; 544/298; 544/300; 544/310; 544/316; 544/317; 544/319; 544/320; 544/321; 544/322; 544/324; 544/328; 544/331; 544/333; 544/359; 544/364; 544/371; 544/405; 546/193; 546/194; 546/211; 546/256; 546/277; 546/279; 548/122; 548/123; 548/124; 548/125; 548/127; 548/128; 548/129; 548/131; 548/132; 548/133; 548/134; 548/135; 548/137; 548/143; 548/144; 548/182; 548/183; 548/184; 548/186; 548/189; 548/190; 548/191; 548/193; 548/202; 548/203; 548/213; 548/214; 548/225; 548/226; 548/227; 548/228; 548/229; 548/230; 548/232; 548/233; 548/235; 548/237; 548/238; 548/239; 548/245; 548/246; 548/247; 548/249; 548/255; 548/262; 548/263; 548/266; 548/269; 548/300; 548/336; 548/348; 548/362

[58] Field of Search ............... 548/362, 122, 123, 124, 548/125, 127, 128, 129, 131, 132, 133, 134, 135, 137, 143, 144, 182, 183, 184, 186, 189, 190, 191, 193, 202, 203, 213, 214, 225, 226, 227, 228, 229, 230, 232, 233, 235, 237, 238, 239, 245, 246, 247, 249, 255, 262, 266, 269, 300, 336, 348; 71/92, 90; 544/2, 5, 7, 8, 55, 56, 60, 63, 65, 66, 67, 96, 98, 124, 131, 140, 182, 198, 207, 212, 217, 218, 219, 238, 298, 300, 310, 316, 317, 319, 320, 321, 322, 324, 328, 331, 333, 359, 364, 371, 405; 546/193, 194, 211, 256, 277, 279

[56] References Cited

U.S. PATENT DOCUMENTS 4,459,150 7/1984 Hatton et al. ..................... 548/362

Primary Examiner—Henry R. Jiles
Assistant Examiner—Kurt G. Briscoe
Attorney, Agent, or Firm—Sprung Horn Kramer & Woods

[57] ABSTRACT

1-Aryl-5-alkoximinoalkylamino-pyrazoles of the formula

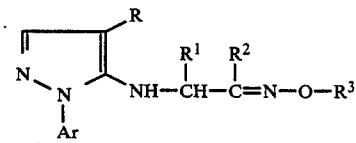

in which
R represents cyano or nitro, or represents an optionally substituted heterocyclic radical,
$R^1$ represents hydrogen or alkyl,
$R^2$ represents hydrogen or alkyl, or represents optionally substituted aryl,
$R^3$ represents hydrogen, alkyl or alkenyl, or represents in each case optionally substituted aralkyl or aryl and
Ar represents optionally substituted phenyl or pyridyl, are active as herbicides and plant growth regulants. Compounds of the formula

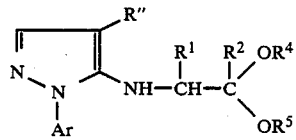

in which R'' has the same definition as R other than cyano, are also active and useful as intermediates as well.

10 Claims, No Drawings

1-ARYL-5-ALKOXIMINOALKYLAMINO-PYRAZOLES, COMPOSITION CONTAINING THEM, HERBICIDAL AND PLANT-GROWTH REGULATING METHOD OF USING THEM, AND INTERMEDIATES IN THE PREPARATION OF THEM

The invention relates to new 1-aryl-5-alkoximinoalkylamino-pyrazoles, several processes for their preparation and their use as herbicides and growth regulators.

It is already known that certain 1-aryl-5-aminopyrazoles, such as, for example, 4-cyano-5-propionamido-1-(2,3,4-trichlorophenyl)-pyrazole, have herbicidal properties (compare, for example, DE-OS (German Published Specification) No. 3,226,513.

However, the herbicidal activity of these already known compounds against weeds, like their tolerance towards important useful plants, is not always completely satisfactory in all fields of use.

Nothing is known of use of the already known compounds as growth regulators.

New 1-aryl-5-alkoximinoalkylamino-pyrazoles of the general formula (I)

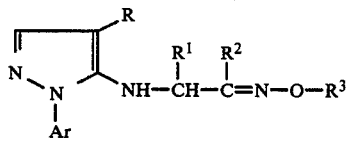

in which
R represents cyano or nitro, or represents an optionally substituted heterocyclic radical,
$R^1$ represents hydrogen or alkyl,
$R^2$ represents hydrogen or alkyl, or represents optionally substituted aryl,
$R^3$ represents hydrogen, alkyl or alkenyl, or represents in each case optionally substituted aralkyl or aryl and
Ar represents optionally substituted phenyl or pyridyl,
have been found.

It has furthermore been found that the new 1-aryl-5-alkoximinoalkylamino-pyrazoles of the formula (I)

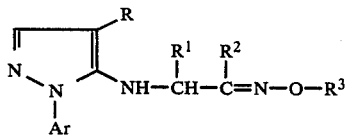

in which
R represents cyano or nitro, or represents an optionally substituted heterocyclic radical,
$R^1$ represents hydrogen or alkyl,
$R^2$ represents hydrogen or alkyl, or represents optionally substituted aryl,
$R^3$ represents hydrogen, alkyl or alkenyl, or represents in each case optionally substituted aralkyl or aryl and
Ar represents optionally substituted phenyl or pyridyl,
are obtained by a process in which
(a) 5-amino-1-aryl-pyrazoles of the formula (II)

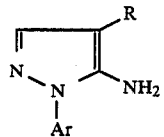

in which R and Ar have the abovementioned meaning, are reacted with alkoximinoalkyl halides of the formula (III)

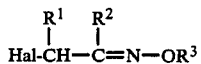

in which
$R^1$, $R^2$ and $R^3$ have the abovementioned meaning and Hal represents halogen,
if appropriate in the presence of a diluent and if appropriate in the presence of an acid-binding agent, or in which
(b) 5-dialkoxyalkylamino-pyrazoles of the formula (IV)

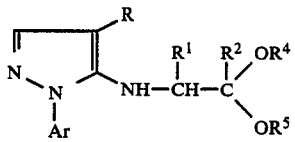

in which
R, $R^1$, $R^2$ and Ar have the abovementioned meaning and
$R^4$ and $R^5$ represent alkyl,
are reacted with hydroxylamine derivatives of the formula (V)

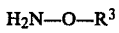

in which $R^3$ has the abovementioned meaning, or acid addition salts thereof, if appropriate in the presence of a diluent and if appropriate in the presence of an acid-binding agent.

Finally, it has been found that the new 1-aryl-5-alkoximinoalkylamino-pyrazoles of the formula (I) have herbicidal properties, and in particular also selective herbicidal properties, and plant growth regulatory properties.

Surprisingly, the 1-aryl-5-alkoximinoalkylamino pyrazoles of the general formula (I) according to the invention simultaneously show, in addition to a considerably improved herbicidal activity against problem weeds, a clearly higher selectivity towards important crop plants than the 1-aryl-5-amino-pyrazoles known from the prior art, such as, for example, 4-cyano-5-propionamido-1-(2,3,4-trichlorophenyl)-pyrazole, which are closely related compounds chemically and from the point of view of their action. Surprisingly, the compounds of the formula (I) according to the invention also show a good activity as growth regulators.

Formula (I) provides a general definition of the 1-aryl-5-alkoximinoalkylamino-pyrazoles according to the invention.

Preferred compounds of the formula (I) are those in which
R represents cyano or nitro, or represents a saturated or unsaturated, five-membered or six-membered heterocyclic radical which is optionally monosubstituted or polysubstituted by identical or different substituents, contains one to three identical or different hetero atoms from the group comprising nitrogen, oxygen and sulphur and can be linked via a carbon or a nitrogen atom, the substituents chosen being: halogen, nitro and in each case straight-chain or branched alkyl, alkoxy or alkylthio with in each case 1 to 4 carbon atoms or halogenoalkyl with 1 to 4 carbon atoms and 1 to 9 identical or different halogen atoms, R¹ represents hydrogen, or represents straight-chain or branched alkyl with 1 to 8 carbon atoms, R² represents hydrogen, or represents straight-chain or branched alkyl with 1 to 8 carbon atoms, or represents phenyl which is optionally monosubstituted or polysubstituted by identical or different substituents, the substituents chosen being: halogen, cyano, nitro, in each case straight-chain or branched alkyl, alkoxy, alkylthio or alkoxycarbonyl with in each case 1 to 4 carbon atoms in the individual alkyl parts or in each case straight-chain or branched halogenoalkyl, halogenoalkoxy or halogenoalkylthio with in each case 1 to 4 carbon atoms and 1 to 9 identical or different halogen atoms, R³ represents hydrogen, or represents straight-chain or branched alkyl with 1 to 8 carbon atoms, or represents straight-chain or branched alkenyl with 3 to 8 carbon atoms, or represents benzyl or phenyl, in each case optionally monosubstituted or polysubstituted by identical or different substituents from the group comprising halogen, cyano, nitro and in each case straight-chain or branched alkyl, alkoxy and alkylthio with in each case 1 to 4 carbon atoms and halogenoalkyl with 1 to 4 carbon atoms and 1 to 9 identical or different halogen atoms and Ar represents phenyl, 2-pyridyl, 3-pyridyl or 4-pyridyl, in each case optionally monosubstituted or polysubstituted by identical or different substituents, the substituents chosen being: cyano, nitro, halogen, in each case straight-chain or branched alkyl, alkoxy or alkoxycarbonyl with 1 to 4 carbon atoms in the individual alkyl parts, in each case straight-chain or branched halogenoalkyl or halogenoalkoxy with in each case 1 to 4 carbon atoms and 1 to 9 identical or different halogen atoms or a radical —S(O)$_n$—R⁶, wherein R⁶ represents amino, or represents in each case straight-chain or branched alkyl, alkylamino or dialkylamino with in each case 1 to 4 carbon atoms in the individual alkyl parts or halogenoalkyl with 1 to 4 carbon atoms and with 1 to 9 identical or different halogen atoms and n represents the number 0, 1 or 2.

Particularly preferred compounds of the formula (I) are those in which R represents cyano or nitro, or represents a heterocylic radical of the formula

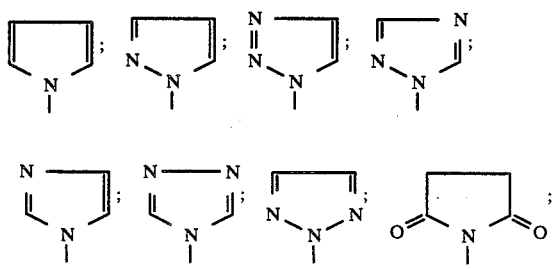

-continued

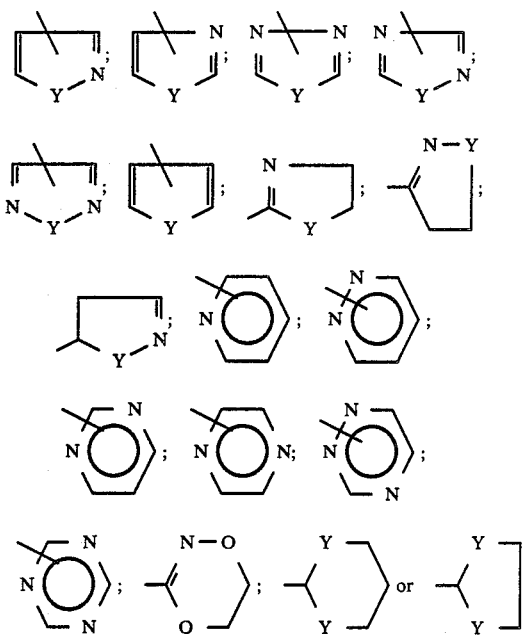

in each case optionally mono-, di- or trisubstituted by identical or different substituents from the group comprising fluorine, chlorine, bromine, nitro, methyl, ethyl, n- and i-propyl, methoxy, ethoxy, n- and i-propoxy, methylthio, ethylthio, n- and i-propylthio and trifluoromethyl, wherein Y in each case represents oxygen, sulphur or an N-alkyl radical with 1 to 4 carbon atoms, R¹ represents hydrogen, methyl, ethyl, n- or i-propyl or n-, i-, s- or t-butyl, R² represents hydrogen, methyl, ethyl, n- or i-propyl or n-, i-, s- or t-butyl, or represents phenyl which is optionally mono-, di- or trisubstituted by, identical or different substituents from the group comprising fluorine, chlorine, bromine, cyano, nitro, methyl, ethyl, methoxy, ethoxy, methylthio, ethylthio, methoxycarbonyl, ethoxycarbonyl, trifluoromethyl, trifluoromethoxy and trifluoromethylthio, R3 represents hydrogen, methyl, ethyl, n- or i-propyl, n-, i-, s- or t-butyl, allyl, 2-butenyl or 2-methyl-2-butenyl, or represents benzyl or phenyl, in each case mono-, di- or trisubstituted by identical or different substituents, the substituents chosen in each case being: fluorine, chlorine, bromine, cyano, nitro, methyl, ethyl, methoxy, ethoxy, methylthio, ethylthio or trifluoromethyl and Ar represents phenyl, 2-pyridyl or 4-pyridyl, in each case optionally mono-, di-, tri-, tetra- or pentasubstituted by identical or different substituents, the substituents chosen being: cyano, nitro, fluorine, chlorine, bromine, iodine, methyl, ethyl, n- and i-propyl, n-, i-, s- and t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy or a radical —S(O)$_n$—R$^6$, wherein R$^6$ represents amino, methyl, ethyl, methylamino, ethylamino,, dimethylamino, diethylamino, fluorodichloromethyl, difluoromethyl, tetrafluoroethyl, trifluorochloroethyl or trifluoromethyl and n represents the number 0, 1 or 2.

The following 1-aryl-5-alkoximinoalkylaminopyrazoles of the general formula (I) may be mentioned specifically, in addition to the compounds mentioned in the preparation examples:

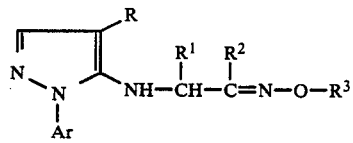
(I)

| R | R$^1$ | R$^2$ | R$^3$ | Ar |
|---|---|---|---|---|
| CN | CH$_3$ | H | CH$_3$ | 3,5-dichloro-pyrid-2-yl with CF$_3$ |
| NO$_2$ | CH$_3$ | H | CH$_3$ | 3,5-dichloro-pyrid-2-yl with CF$_3$ |
| CN | CH$_3$ | H | CH$_3$ | 2-Cl,4-CF$_3$-phenyl |
| NO$_2$ | CH$_3$ | H | CH$_3$ | 2-Cl,4-CF$_3$-phenyl |
| CN | CH$_3$ | H | CH$_3$ | 2,6-diCl,4-CF$_3$-phenyl |
| NO$_2$ | CH$_3$ | H | CH$_3$ | 2,6-diCl,4-CF$_3$-phenyl |
| CN | CH$_3$ | H | CH$_3$ | 2,6-diCl,4-SO$_2$CF$_3$-phenyl |
| CN | CH$_3$ | H | CH$_3$ | 2,6-diCl,4-SO$_2$CF$_3$-phenyl (triazole variant) |
| CN | CH$_3$ | H | CH$_3$ | triazolyl-2,6-diCl,4-CF$_3$-phenyl |

If, for example, 5-amino-4-cyano-1-(2,6-dichloro-4-trifluoromethylphenyl)-pyrazole and 2-bromo-1-methoximino-propane are used as starting substances, the course of the reaction in process (a) according to the invention can be represented by the following equation:

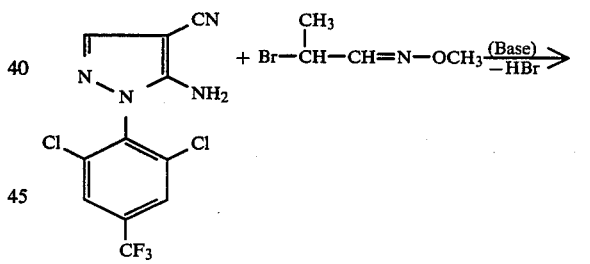

If, for example, 4-cyano-1-(3,5-dichloro-pyrid-2-yl)-5-(1,1-dimethoxyprop-2-ylamino)-pyrazole and O-methyl-hydroxylamine hydrochloride are used as starting substances, the course of the reaction in process (b) according to the invention can be represented by the following equation:

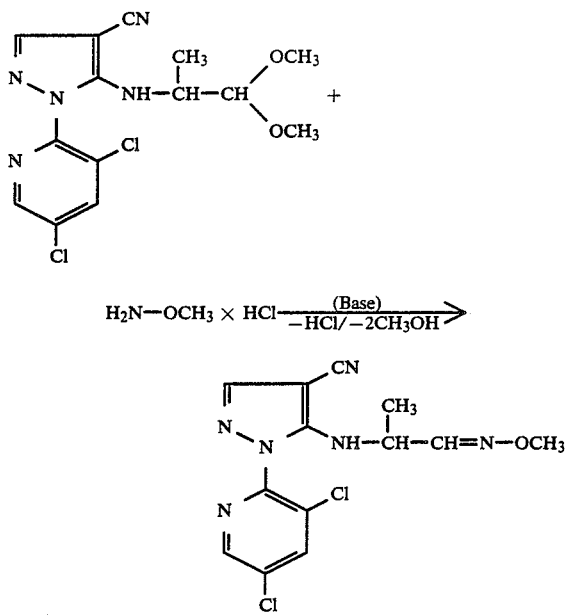

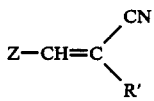

Formula (II) provides a general definition of the 5-amino-1-aryl-pyrazoles required as starting substances for carrying out process (a) according to the invention. In this formula (II), R and Ar preferably represent those radicals which have already been me tioned as preferred for these substituents in connection with the description of the substances of the formula (I) according to the invention.

The 5-amino-1-aryl-pyrazoles of the formula (II) are known in some cases (compare, for example, European Patent No. 26,034, European Patent No. 53,678, European Patent No. 34,945, DE-OS (German Published Specification) No. 3,226,496 or DE-OS (German Published Specification) No. 3,408,727), and some of them are the subject of commonly assigned applications Serial No. 690,347, filed Jan. 10, 1985, now pending, corresponding to German Patent No. 3,402,308 of Jan. 24, 1984, German Patent No. 3,423,101 of June 22, 1984 and German Patent No. 3,420,985 of June 6, 1984.

Compounds of the formula (II) in which R represents cyano or represents an optionally substituted heterocyclic radical are obtained by a process in which arylhydrazines of the formula (VI)

Ar—NH—NH$_2$     (VI)

in which Ar has the abovementioned meaning, are initially reacted in a 1st stage with acrylonitrile derivatives of the formula (VIIa)

in which

R' represents cyano, or represents an optionally substituted heterocyclic radical and Z represents halogen, hydroxyl, alkoxy or dialkylamino, if appropriate in the presence of a diluent, such as, for example, glacial acetic acid or ethanol, and if appropriate in the presence of a reaction auxiliary, such as, for example, sodium acetate, at temperatures between −20° and +20° C., to give the arylhydrazine derivatives of the formula (VIII)

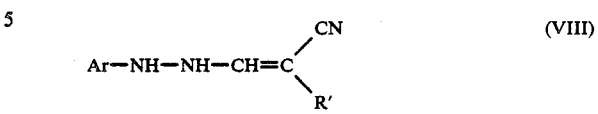

in which Ar and R' have the abovementioned meaning, and the intermediate products of the formula (VIII) are cyclized in a 2nd stage, if appropriate in the presence of a diluent, such as, for example, ethylene glycol monoethyl ether, and if appropriate in the presence of an acid catalyst, such as, for example, sulphuric or phosphoric acid, at temperatures between +50° and +150° C.

The reaction can also be carried out directly in one reaction step without isolation of the intermediate products of the formula (VIII), if appropriate in the presence of a diluent, such as, for example, ethylene glycol monoethyl ether or ethanol, at temperatures between +50° and +150° C.

Compounds of the formula (II) in which R represents nitro are obtained by a process in which arylhydrazines of the formula (VI)

Ar—NH—NH$_2$     (VI)

in which Ar has the abovementioned meaning, are reacted with 2-halogenoacrylonitriles of the formula (VIIb)

in which Hal represents halogen, in particular chlorine or bromine, by the procedure described above, either in a two-stage or in a one-stage reaction, to give the 5-amino-pyrazoles unsubstituted in the 4-position, of the formula (IX)

in which Ar has the abovementioned meaning, and these are nitrated in the 4-position of the pyrazole ring in a subsequent reaction with a nitrating agent, such as, for example, nitric acid, if appropriate in the presence of a diluent, such as, for example, glacial acetic acid, and if appropriate in the presence of a reaction auxiliary, such as, for example, acetic anhydride, at temperatures between −20° and +50° C.

If appropriate, it may furthermore be of advantage to protect the amino group in the 5-position of the pyrazole ring from the nitration reaction with the aid of a protective group, for example by acylation, and, after the nitration has been carried out, to split off the protective group again, for example by hydrolysis with an aqueous or alcoholic base.

Formula (III) provides a general definition of the alkoximinoalkyl halides furthermore required as starting substances for carrying out process (a) according to the invention. In this formula (III), $R^1$, $R^2$ and $R^3$ preferably represent those radicals which have already been mentioned as preferred for these substituents in connection with the description of the substances of the formula (I) according to the invention.

The alkoximinoalkyl halides of the formula (III) are known (compare, for example, DE-OS (German Published Specification) No. 2,922,759 or U.S. Pat. No. 4,337,268), or they can be prepared by known processes in a simple analogous manner.

The arylhydrazines of the formula (VI) are likewise known (compare, for example, U.S. Pat. Nos. 4,127,575; 3,609,158; DE-OS (German Published Specification) No. 2,558,399; and J. chem. Soc. C, 167–174 (1971)), or they can be obtained by known processes in a simple analogous manner (compare, for example, Houben-Weyl "Methoden der organischen Chemie" ("Methods of Organic Chemistry"), Volume X/2 page 203, Thieme Verlag Stuttgart, (1967)), for example by a procedure in which the compounds of the formula (X)

    Ar—NH$_2$     (X)

in which Ar has the abovementioned meaning, are reacted with sodium nitrite in the presence of an acid, such as, for example, sulphuric acid, and then with tin-II chloride, likewise in the presence of an acid, such as, for example, hydrochloric acid, at temperatures between −20° C. and +80° C., or in which compounds of the formula (XI)

Ar—Hal$^2$     (XI)

in which

Ar has the abovementioned meaning and

Hal$^2$ represents halogen, in particular fluorine, chlorine or bromine, are reacted with hydrazine hydrate, if appropriate in the presence of a diluent, such as, for example, pyridine or dioxane, at temperatures between 0° C. and +150° C.

The acrylonitrile derivatives of the formula (VIIa), the 2-halogenoacrylonitriles of the formula (VIIb), the compounds of the formula (X) and compounds of the formula (XI) are generally known compounds of organic chemistry.

Formula (IV) provides a general definition of the 5-dialkoxyalkylamino-pyrazoles required as starting substances for carrying out process (b) according to the invention. In this formula (IV), R, $R^1$, $R^2$ and Ar preferably represent those radicals which have already been mentioned as preferred for these substituents in connection with the description of the substances of the formula (I) according to the invention.

$R^4$ and $R^5$ preferably represent straight-chain or branched alkyl with 1 to 4 carbon atoms, in particular methyl or ethyl.

The 5-dialkoxyalkylamino-pyrazoles of the formula (IV) in which R represents cyano are the subject of commonly assigned application Ser. No. 754,048, filed July 11, 1985 now pending, corresponding to German Patent application P3 426 424 of July 18, 1984.

The 5-dialkoxyalkylamino-pyrazoles of the formula (IV) in which R represents nitro or represents an optionally substituted heterocyclic radical are new, and formula (IVa)

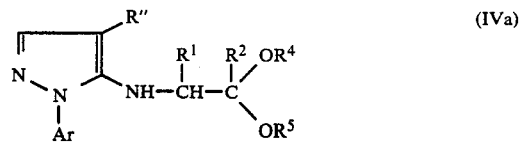

provides a general definition of them. In formula (IVa),

R" represents, nitro, or represents an optionally substituted heterocyclic radical, $R^1$ represents hydrogen or alkyl, $R^2$ represents hydrogen or alkyl, or represents optionally substituted aryl, $R^4$ represents alkyl, $R^5$ represents alkyl and Ar represents optionally substituted phenyl or pyridyl.

In formula (IVa), R" preferably has the meaning of R, with the exception of cyano, which has already been mentioned as preferred for these substituents in connection with the description of the substances of the formula (I) according to the invention, and $R^1$, $R^2$ and Ar have those meanings which have already been mentioned as preferred for $R^1$, $R^2$ and Ar in connection with the description of the substances of the formula (I) according to the invention. $R^4$ and $R^5$ preferably represent straight-chain or branched alkyl with 1 to 4 carbon atoms, in particular methyl or ethyl.

In formula (IVa), R", $R^1$, $R^2$ and Ar particularly preferably have those meanings of R (with the exception of cyano), $R^1$, $R^2$ and Ar which have already been mentioned as particularly preferred for these substituents in connection with the description of the substances of the formula (I) according to the invention.

Compounds of the formula (IVa) are obtained by a process in which 5-amino-1-aryl-pyrazoles of the formula (IIa)

in which

R" represents nitro, or represents an optionally substituted heterocyclic radical and Ar represents optionally substituted phenyl or pyridyl, are diazotized with nitrite compounds of the formula (XII)

    R$^7$—O—N=O     (XII)

in which R$^7$ represents hydrogen, an alkali metal cation or alkyl, in the presence of a hydrogen halide acid or in the presence of a haloform and a catalyst acid, such as, for example, sulphuric acid, at temperatures between −20° C. and 80° C., and the 5-halogenopyrazoles thus obtainable, of the formula (XIII)

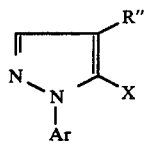

in which

R″ and Ar have the abovementioned meaning and
X represents halogen, in particular chlorine or bromine, are reacted with dialkoxyalkylamines of the formula (XIV)

in which $R^1$, $R^2$, $R^4$ and $R^5$ have the abovementioned meaning, at temperatures between $+50°$ C. and $+250°$ C.

The diazotization of the compounds of the formula (IIa) is carried out in the customary manner (compare "Organikum" 15th edition, VEB Deutscher Verlag der Wissenschaften, Berlin 1981, page 652 et seq; and J. chem. Soc. C 1249 (1966), Rev. Latinoam. Quim. 13, 100–102 (1982)).

All the compounds of the formula (IV) can be prepared by the process described above.

The 5-amino-1-aryl-pyrazoles of the formula (IIa) are known in some cases (compare, for example, European Patent No. 26,034, European Patent No. 53,678 or DE-OS (German Publisher Specification) No. 3,408,727), and some of them are the subject of commonly assigned applications Serial No. 690,347, filed Jan. 10, 1985, now pending, corresponding to German Patent No. 3,402,308 of Jan. 24, 1984, and German Patent No. 3,423,101 of June 22, 1984 and German Patent No. 3,420,985 of June 6, 1984.

In formula (IIa), R″ and Ar preferably or partcularly preferably have those meanings of R (with the exception of cyano) and Ar which have already been mentioned as preferred or particularly preferred for these substituents in connection with the description of the substances of the formula (I) according to the invention.

The 5-amino-1-aryl-pyrazoles of the formula (IIa) are obtainable by the same processes which have been described for the preparation of the 5-amino-1-aryl-pyrazoles of the formula (II).

The nitrite compounds of the formula (XII) and the dialkoxyalkylamines of the formula (XIV) are generally known compounds of organic chemistry. The 5-halogenopyrazoles of the formula (XIII), obtainable as intermediate products, are the subject of commonly assigned applications Serial No. 816,643, filed Jan. 6, 1986, now pending, corresponding to German application No. P 3,501,323 of Jan. 17, 1985, and alternatively are also obtainable by the preparation methods described therein.

Formula (V) provides a general definition of the hydroxylamine derivatives furthermore required as starting substances for carrying out process (b) according to the invention. In this formula (V), $R^3$ preferably represents those radicals which have already been mentioned as preferred for these substituents in connection with the description of the substances of the formula (I) according to the invention.

The hydroxylamine derivatives of the formula (V) and acid addition salts thereof are generally known compounds of organic chemistry.

Possible diluents for carrying out process (a) according to the invention are inert organic solvents.

These include, in particular, aliphatic or aromatic, optionally halogenated hydrocarbons, such as, for example, benzine, benzene, toluene, xylene, chlorobenzene, petroleum ether, hexane, cyclohexane, methylene chloride, chloroform or carbon tetrachloride, ethers, such as diethyl ether, dioxane, tetrahydrofuran or ethylene glycol dimethyl or diethyl ether, ketones, such as acetone or butanone, nitriles, such as dimethylformamide, dimethylacetamide, N-methylformamilide, N-methylpyrrolidone or hexamethylphosphoric acid triamide, esters, such as ethyl acetate, or sulphoxides, such as dimethylsulphoxide.

If appropriate, process (a) according to the invention is carried out in the presence of a suitable acid-binding agent.

Possible acid-binding agents are all the customary inorganic or organic bases. These include, for example, alkali metal hydroxides, such as sodium hdroxide or potassium hydroxide, alkali metal carbonates, such as sodium carbonate, potassium carbonate or sodium bicarbonate, and tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

The reaction temperatures can be varied within a substantial range in carrying out process (a) according to the invention. The reaction is in general carried out at temperatures between $0°$ C. and $+150°$ C., preferably at temperatures between $+20°$ C. and $+120°$ C.

For carrying out process (a) according to the invention, in general 1 to 10 moles, preferably 1 to 5 moles, of alkoximinoalkyl halide of the formula (III) and, if appropriate, 1 to 5 moles, preferably 1 to 2.5 moles, of acid-binding agent are employed per mole of 5-amino-1-aryl-pyrazole of the formula (II).

The reaction is carried out and the reaction products of the formula (I) are worked up and isolated by customary processes.

Possible diluents for carrying out process (b) according to the invention are likewise inert organic solvents.

The solvents or alcohols listed for process (a), such as methanol or ethanol, are preferably used.

The reaction temperatures can be varied within a substantial range in carrying out process (b) according to the invention. The reaction is in general carried out at temperatures between $0°$ C. and $+150°$ C., preferably at temperatures between $+20°$ C. and $+100°$ C.

For carrying out process (b) according to the invention, in general 1 to 3 moles, preferably 1 to 1.5 moles, of hydroxylamine derivative of the formula (V) and, if appropriate, 1 to 3 moles, preferably 1 to 1.5 moles, of acid-binding agent are employed per mole of 5-dialkoxyalkyl-amino-pyrazole of the formula (IV).

The reaction is carried out and the reaction products of the formula (I) are worked up and isolated by customary methods.

The active compounds according to the invention can be used as defoliants, desiccants, agents for destroying broad-leaved plantS and, eSpecially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds of the formula (I) according to the invention can furthermore be employed with particularly good success for selectively combating monocotyledon and dicotyledon weeds in monocotyledon and dicotyledon crops, such as, for example, wheat and cotton.

The precursors of the formula (IV) also exhibit a good herbicidal activity.

The active compounds according to the invention engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the Crop plants in the particular manner desired.

Plant growth-regulating compounds can be employed, for example, to inhibit vegetative growth of the plants. Such inhibition of growth is, inter alia, of economic interest in the case of grasses, since it is thereby possible to reduce the frequency of cutting the grass in ornamental gardens, parks and sportsgrounds, at verges, at airports or in fruit orchards. The inhibition of growth of herbaceous and woody plants at verges and in the vicinity of pipelines or overland lines or, quite generally, in areas in which heavy additional growth of plants is undesired, is also of importance.

The use of growth regulators to inhibit the growth in length of cereals is also important. The danger of bending ("lodging") of the plants before harvesting is thereby reduced or completely eliminated. Furthermore, growth regulators can strengthen the stem of cereals, which again counteracts lodging. Use of growth regulators for shortening and strengthening the stem enables higher amounts of fertilizer to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beet, sugar cane, pineapples and citrus fruit or to increase the protein content in soya or cereals. Using growth regulators it is also possible, for example, to inhibit the degradation of desired constituents, such as, for example, sugar in sugar beet or sugar cane, before or after harvesting. It is also possible favorably to influence the production or the efflux of secondary plant constituents. The stimulation of latex flux in rubber trees may be mentioned as an example.

Parthenocarpous fruits can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can also be promoted up to a certain degree ("thinning out") in order to interrupt the alternance. By alternance there is understood the peculiarity of some varieties of fruit to produce very different yields from year to year, for endogenic reasons. Finally, using growth regulators it is possible to reduce the forces required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants, such as, for example, pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants to frost, drought or a high salt content in the soil can be induced with growth regulators. Cultivation of plants in regions which are usually unsuitable for this purpose thereby becomes possible.

The active compounds of the formula (I) according to the invention moreover also have an insecticidal activity.

The active compounds can be converted to the customary formulations, such as solutions, emulsions, suspensions, powders, foams, pastes, granules, aerosols, very fine capsules in polymeric substances and in coating compositions positions for seed, as well as ULV formulations.

These formulations are produced in a known manner, for example by mixing the active compounds with extenders, that is, liquid solvents, liquefied gases under pressure, and/or solid carriers, optionally with the use of surface-active agents, that is, emulsifying agents and-/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example, ground natural minerals, such as kaolins, clays, talc, chalk, quartz, attapulgite, montmorillonite or diatomaceous earth, and ground synthetic minerals, such as highly dispersed silicic acid, alumina and silicates. As solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example, non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products. As dispersing agents there are suitable: for example, ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as such or as a mixture with other known active compounds, such as fungicides, insecticides, nematicides, acaricides and other herbicides, and also as mixtures with fertilizers, bird repellents, agents which improve soil structure and other growth regulators, finished formulations or tank mixes being possible.

Possible components for the mixtures with other herbicides are known herbicides, such as, for example, 1-amino-6-ethylthio-3-(2,2-dimethylpropyl)-1,3,5-triazine-2,4(1H, 3H)dione or N-(2-benzothiazolyl)-N,N'-dimethylurea, for combating weeds in cereals; 4-amino-3-methyl-6-phenyl-1,2,4-triazin-5-(4H)-one, for combating weeds in sugar beet, and 4-amino-6-(1,1-dimethylethyl)-3-methylthio-1,2,4-triazin-5(4H)-one for combating weeds in soya bean.

Mixtures with N,N-dimethyl-N'-(3-trifluoromethylphenyl)-urea; N,N-dimethyl-N'-(3-chloro-4-methylphenyl)urea; N,N-dimethyl-N'-(4-isopropylphenyl)-urea; 4-amino-6-t-butyl-3-ethylthio-1,2,4-triazin-5(4H)-one; 2,4-dichlorophenoxyacetic acid; 2,4-dichlorophenoxypropionic acid; (2-methyl-4-chlorophenoxy)-acetic acid; (4-chloro-2-methylphenoxy)-propionic acid; chloroacetic acid N-(methoxy-methyl)-2,6-diethylanilide; 2-ethyl-6-methyl-N-(1-methyl-2-methoxyethyl)-chloroacetanilide; methyl 5-(2,4-dichlorophenoxy)-2-nitrobenzoate; 3,5-diiodo-4-hydroxybenzonitrile; 3-isopropyl-2,1,3-benzothiadiazin-4-one 2,2-dioxide; 2-chloro-N-{[(4-methoxy-6-methyl-1,3,5-triazan-2-yl)-amino]-carbonyl}-benzenesulphonamide; 4-ethylamino-2-t-butylamino-6-methylthio-S-triazine; N-(1-ethylpropyl)-3,4-dimethyl2,6-dinitroaniline; 6-chloro-3-phenyl-pyridazin-4-yl Soctyl thiocarbonate; S-(2,3,3-trichloroallyl) N,N-diisopropyl-thiocarbamate; N-methyl-2-(1,3-benzothiazol-2-yloxy)acetanilide; S-ethyl N,N-di-n-propyl-thiocarbamate; exo-1-methyl-4-(1-methylethyl)-2-(2-methylphenylmethoxy)-7-oxabicydo-[2.2.1]-heptane; 2-{4- [[3-chloro-5-(trifluoromethyl)-2-pyridinyl]-oxy]-phenoxy}-propanoic acid or -propanoic acid ethyl ester; [(4-amino-3,5-dichloro-6-fluoro-2-pyridinyl)-oxy]-acetic acid or -acetic acid 1-methylheptyl ester; 3,5-dibromo-4-hydroxy-benzonitrile; methyl 2-[4(2,4-dichlorophenoxy)-phenoxy]-propionate; 4,6-dinitro-2-(1-methylpropyl)-phenol; 2,6-dinitro-4-trifluoromethyl-N,N-dipropylaniline; and 2-benzyloxyethyl, trimethylsilylmethyl or 2,2-diethoxyethyl 2-[4-(3,5-dichloropyrid-2-yloxy)phenoxy]propionate; are also of advantage, where appropriate.

Surprisingly, some mixtures also exhibit a synergistic action.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming, coating and the like. Furthermore, it is possible to apply the active compounds in accordance with the ultra-low volume process or to inject the active compound preparation or the active compound itself into the soil. It is also possible to treat the seeds of the plants.

The active compounds according to the invention can be applied either before or after emergence of the plants.

They can also be incorporated into the soil before sowing.

The amount of active compound applied can vary within a substantial range. It depends essentially on the nature of the desired effect. In general, the amounts used are between 0.01 and 10 kg of active compound per hectare of soil surface, preferably between 0.05 and 5 kg per ha.

When used as growth regulators, the application period depends on the climatic and vegetative circumstances.

The preparation and use of the active compounds according to the invention can be seen from the following examples.

PREPARATION EXAMPLES

Example 1

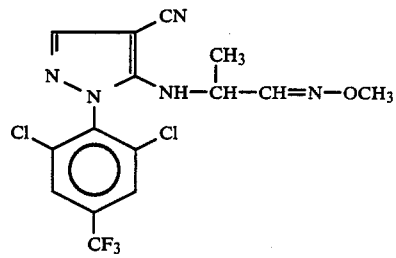

(Process a)

10.5 g (0.033 mole) of 5-amino-4-cyano-1-(2,6-dichloro-4-trifluoromethylphenyl)-pyrazole, 9.1 g (0.066 mole) of potassium carbonate and 12.7 g (0.073 mole) of 2-bromo-1-methoximinopropane in 100 ml of acetonitrile are heated under reflux until the starting substance is no longer detectable in the thin layer chromatogram (period of about 2 days). The cooled reaction mixture is filtered, volatile constituents are distilled off in vacuo at a bath temperature of 70° C. and the oily residue is crystallized with petroleum ether.

11.1 g (83% of theory) of 4-cyano-5-(1-methoximino-prop-2-ylamino)-1-(2,6-dichloro-4-trifluoromethylphenyl)pyrazole of melting point 117° C.–119° C. are obtained.

The following 1-aryl-5-alkoximino-alkylaminopyrazoles of the general formula (i) are obtained in a corresponding manner and in accordance with the general instructions on the preparation:

TABLE 1

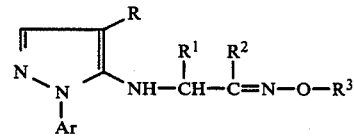

| Example No. | R | R¹ | R² | R³ | Ar | Physical properties |
|---|---|---|---|---|---|---|
| 2 | CN | CH₃ | H | CH₃ | 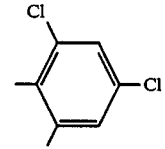 | Melting point 121° C. |
| 3 | NO₂ | CH₃ | H | CH₃ | 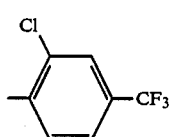 | Melting point 81° C. |
| 4 | CN | CH₃ | H | CH₃ | 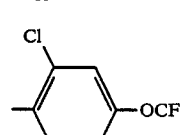 | Melting point 112-115° C. |

TABLE 1-continued

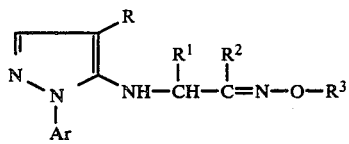  (I)

| Example No. | R | R¹ | R² | R³ | Ar | Physical properties |
|---|---|---|---|---|---|---|
| 5 | CN | H | H | CH₃ | 3,5-dichloro-4-CF₃-phenyl | ¹H—NMR 3.7 ppm* |
| 6 | CN | CH₃ | H | CH₃ | 3-chloro-4-OCF₃-phenyl | ¹H—NMR 3.7 ppm* |
| 7 | CN | CH₃ | H | CH₃ | 3,5-dichloro-4-SCF₃-phenyl | ¹H—NMR 3.7 ppm* |
| 8 | CN | CH₃ | H | CH₃ | 2,6-dichloro-4-SCF₃-phenyl | ¹H—NMR 3.7 ppm* |
| 9 | CN | CH₃ | H | CH₃ | 2,6-dichloro-4-OCF₃-phenyl | ¹H—NMR 3.7 ppm* |
| 10 | NO₂ | CH₃ | H | CH₃ | 2,6-dichloro-4-SCF₃-phenyl | ¹H—NMR 3.7 ppm* |
| 11 | NO₂ | CH₃ | H | CH₃ | 2,6-dichloro-4-OCF₃-phenyl | melting point: 83° C. |

TABLE 1-continued

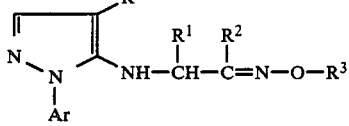  (I)

| Example No. | R | R¹ | R² | R³ | Ar | Physical properties |
|---|---|---|---|---|---|---|
| 12 | CN | CH₃ | H | CH₃ | 3,6-dichloropyridin-2-yl | melting point: 110–120° C. |

*The ¹H—NMR spectra were recorded in chloroform-d₃ with tetramethylsilane as the internal standard. The chemical shift of the methoximino group is given as the δ value in ppm.

USE EXAMPLES

The compound shown below was employed as the comparison substance in the use examples:

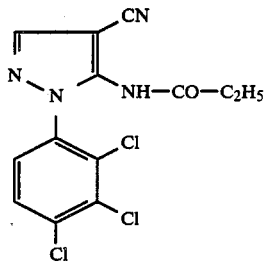  (A)

4-cyano-5-propionamido-1-(2,3,4-trichlorophenyl)-pyrazole (known from DE-OS (German Published Specification) No. 3,226,513).

Example A

Pre-emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% =no action (like untreated control)
100% =total destruction

In this test, a clearly superior activity and crop plant selectivity compared with the comparison substance (A), is shown, for example, by the compound according to preparation Example 1.

Example B

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, a clearly superior activity and crop plant selectivity compared with the comparison substance (A) is shown, for example, by the compound according to preparation Example 1.

Example C

Defoliation and Desiccation of the Leaves of Cotton

Solvent: 30 parts by weight of dimethylformamide
Emulsifier: 1 parts by weight of polyoxyethylene-sorbitan-mono-laurate To produce a suitable preparation of active compound, 1 part by weight of active compound is mixed with the stated amounts of solvent and emulsifier and the mixture is made up to the desired concentration with water.

Cotton plants are grown in a greenhouse until the 5th secondary leaf has unfolded completely. In this stage, the plants are sprayed with the preparations of active compound until dripping wet. After 1 week, the shedding of leaves and the desiccation of the leaves are rated, in comparison with the control plants.

The figures of merit have the following meanings:
0 denotes no desiccation of leaves, no shedding of leaves
+ denotes slight desiccation of the leaves, slight shedding of leaves
++ denotes severe desiccation of the leaves, severe shedding of leaves
+++ denotes very severe desiccation of the leaves, very severe shedding of leaves.

In this test, a clear superiority in comparison with the untreated control is shown, for example, by the compounds according to preparation Examples 1 and 2.

It will be understood that the specification and examples are illustrative but not limitative of the present invention and that other embodiments within the spirit and scope of the invention will suggest themselves to those skilled in the art.

We claim:

1. A 1-aryl-5-alkoximinoalkylaminopyrazole of the formula

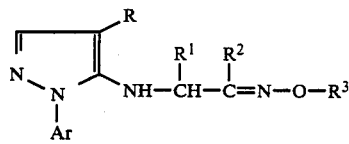

in which

R represents cyano or nitro, or represents of five-membered or six-membered heterocyclic radical which has up to three hetero atoms independently selected from the group consisting of nitrogen, oxygen and sulphur and is optionally sustituted by halogen, nitro, straight-chain or branched alkyl, alkoxy, or alkylthio with in each case 1 to 4 carbon atoms, or halogenoalkyl with 1 to 4 carbon atoms and 1 to 9 halogen atoms, or 2,5-dioxopyrolidinyl $R^1$ represents hydrogen, or represents straight-chain or branched alkyl with 1 to 8 carbon atoms, $R^2$ represents hydrogen, or represents straight-chain or branched alkyl with 1 to 8 carbon atoms, or represents phenyl which is optionally monosubstituted or polysubtituted by identical or different substituents selected from the group consisting of halogen, cyano, nitro, in each case straight-chain or branched alkyl, alkoxy, alkylthio or alkoxy carbonyl with in each case 1 to 4 carbon atoms in the individual alkyl parts or in each case straight-chain or branched halogenoalkyl, halogenoalkoxy or halogenoalkylthio with in each case 1 to 4 carbon atoms and 1 to 9 identical of different halogen atoms, $R^3$ represents hydrogen, or represents straight-chain or branched alkyl with 1 to 8 carbon atoms, or represents straight-chain or branched alkenyl with 3 to 8 carbon atoms, or represents benzyl or phenyl, in each case optionally substituted by identical or different subtituents selected from group consisting of halogen, cyano, nitro, in each case straight-chain or branched alkyl, alkoxy or alkylthio with in each case 1 to 4 carbon atoms, and halogenoalkyl with 1 to 4 carbon atoms and 1 to 9 identical or different halogen atoms and Ar represents phenyl, 2-pyridyl, 3-pyridyl or 4-pyridyl, in each case optionally monosubstituted or polysubstituted by identical or different substituents selected from the group consisting of cyano, nitro, halogen, in each case straight-chain or branched alkyl, alkoxy or alkoxycarbonyl with 1 to 4 carbon atoms in the individual alkyl parts, in each case straight-chain or branched halogenoalkyl or halogenoalkoxy with in each case 1 to 4 carbon atoms and 1 to 9 identical or different halogen atoms or a radical $-S(0)_n-R^6$, wherein $R^6$ represents amino, or represents in each case straight-chain or branched alkyl, alkylamino or dialkylamino with in each case 1 to 4 carbon atoms in the individual alkyl parts, or halogenoalkyl with 1 to 4 carbon atoms and with 1 to 9 identical or different halogen atoms and n represents the number 0, 1 or 2.

2. A 1-aryl-5-alkoximinoalkylamino-pyrazole according to claim 1, in which

R represents cyano or nitro, or represents a heterocyclic radical of the formula

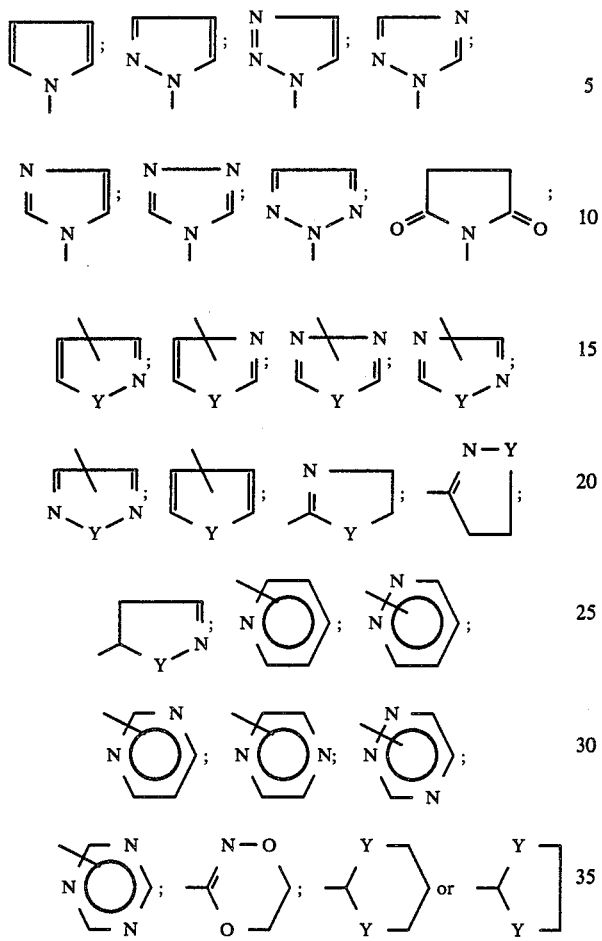

which is optionally mono-, di- or trisubstituted by identical or different substituents selected from the group consisting of fluorine, chlorine, bromine nitro, methyl, ethyl, n- and i-propyl, methoxy, ethoxy, n- and i-propoxy, methylthio, ethylthio, n- and i-propylthio and trifluoromethyl, wherein Y in each case represents oxygen, sulphur or on N-alkyl radical with 1 to 4 carbon atoms, $R^1$ represents hydrogen, methyl, ethyl, n- or i-propyl or n-, i-, s- or t-butyl, $R^2$ represents hydrogen, methyl, ethyl, n- or i-propyl or n-, i-, s- or t-butyl, or represents phenyl which is optionally mono-, di- or trisubstituted by identical or different substituents selected from the group consisting of fluorine, chlorine bromine, cyano, nitro, methyl, ethyl, methoxy, ethoxy, methylthio, ethylthio, methoxycarbonyl, ethoxycarbonyl, trifluoromethyl, trifluoromethoxy and trifluoromethylthio, $R^3$ represents hydrogen, methyl, ethyl, n- or i-propyl, n-, i-, s- or t-butyl, allyl, 2-butenyl or 2-methyl-2-butenyl, or represents benzyl or phenyl, in each case mono-, di- or trisubstituted by identical or different substituents selected from the group consisting of fluorine, chlorine, bromine, cyano, nitro, methyl, ethyl, methoxy, ethoxy, methylthio, ethylthio or trifluoromethyl and Ar represents phenyl, 2-pyridyl or 4-pyridyl, in each case optionally mono-, di-, tri-, tetra- or pentasubstituted by identical or different substituents selected from the group consisting of cyano nitro, fluorine, chlorine, bromine, iodine, methyl, ethyl, n- and i-propyl, n-, i-, s- and t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy or a radical $—S(O)_n—R^6$, $R^6$ represents amino, methyl, ethyl, methylamino, ethylamino, dimethylamino, diethylamino, fluorodichloromethyl, difluoromethyl, tetrafluoroethyl, trifluorochloroethyl or trifluoromethyl and n represents the number 0, 1 or 2.

3. A 1-aryl-5-alkoximinoalkylamino-pyrazole according to claim 1 wherein such compound is 4-cyano-5-(1-methoximinoprop-2-ylamino)-1-(2,6-dichloro-4-trifluoromethylphenyl)pyrazole of the formula

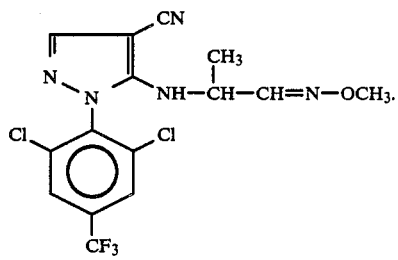

4. A 1-aryl-5-alkoximinoalkylamino-pyrazole according to claim 1, wherein such compound is 4-cyano-5-(1-methoximinoprop-2-yl-amino)-1-(2,3,6-trichloro-4-trifluoromethylthiophenyl)-pyrazole of the formula

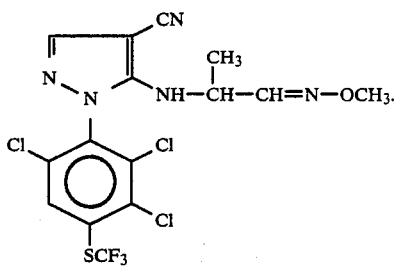

5. A herbicidal and plant growth regulating composition comprising an amount effective therefor of a 1-aryl-5-alkoximinoalkylamino-pyrazole according to claim 1 and a diluent.

6. A method of combating undesired vegetation which comprises applying to such vegetation or to a habitat from which it is desired to exclude such vegetation a herbicidally effective amount of a 1-aryl-5-alkoximinoalkyl-amino-pyrazole according to claim 1.

7. The method according to claim 6 wherein such compound is 4-cyano-5-(1-methoximino-prop-2-ylamino)-1-(2,6-dichloro-4-trifluoromethylphenyl)-pyrazole or 4-cyano-5-(1-methoximino-prop-2-yl-amino)-1-(2,3,6-trichloro-4-trifluoromethylthio-phenyl)-pyrazole.

8. A method of regulating the growth of plants which comprises applying to such plants or to a locus in which such plants are growing or are to be grown a plant-growth regulating effective amount of a 1-aryl-5-alkoximinoalkyl-amino-pyrazole according to claim 1.

9. The method according to claim 8 wherein such compound is
4-cyano-5-(1-methoximino-prop-2-ylamino)-1-(2,6-dichloro-4-trifluoromethylphenyl)-pyrazole or
4-cyano-5-(1-methoximino-prop-2-yl-amino)-1-(2,3,6-trichloro-4-trifluoromethylthiophenyl)-pyrazole.

10. A 5-dialkoxyalkylaminopyrazole of the formula

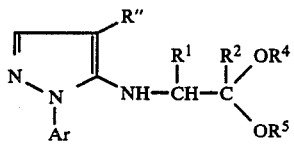

in which
R'', represents nitro, or represents a five-membered or six-membered heterocyclic radical which has up to three hetero atoms independently selected from the group consisting of nitrogen, oxygen and sulphur and is optionally substituted by halogen, nitro, straight-chain or branched alkyl, alkoxy or alkylthio with in each case 1 to 4 carbon atoms, or halogenoalkyl with 1 to 4 carbon atoms and 1 to 9 halogen atoms, or 2,5-dioxopyrrolidinyl, $R^1$ represents hydrogen, or represents straight-chain or branched allkyl with 1 to 8 carbon atoms, $R^2$ represents hydrogen, or presents straight-chain or branched alkyl with 1 to 8 carbon atoms, or represents phenyl which is optionally monosubstituted or polysubstituted by identical or different substituents selected from the group consisting of halogen, cyano, nitro, in each case strasight-chain or branched alkyl, alkoxy, alkylthio or alkoxycarbonyl with in each case 1 to 4 carbon atoms in the individual alkyl parts or in each case straight-chain or branched halogenoalkyl, halogenoalkoxy or halogenalkylthio with in each case 1 to 4 carbon atoms and 1 to 9 identical or different halogen atoms, $R^4$ and $R^5$ represent straight-chain or branched alkyl with 1 to 4 carbon atoms, and Ar represents phenyl, 2-pyridyl, 3-pyridyl or 4-pyridyl, in each case optionally monosubstituted or polysubstituted by identical or different substituents selected from the group consisting of cyano, nitro, halogen, in each case straight-chain or branched alkyl, alkoxy or alkoxycarbonyl with 1 to 4 carbon atoms in the individual alkyl parts, in each case straight-chain or branched halogenoalkyl or halogenoalkoxy with in each case 1 to 4 carbon atoms and 1 to 9 identical or different halogen atoms or a radical —S(O-)$_n$—R$^6$, wherein $R^6$ represents amino, or represents in each case straight-chain or branched alkyl, alkylamino or dialkylamino with in each case 1 to 4 carbon atoms in the individual alkyl parts, or halogenoalkyl with 1 to 4 carbon atoms and with 1 to 9 identical or different halogen atoms and n represents the number 0,1 or 2.

* * * * *

UNITED STATES PATENT AND TRADEMARK OFFICE
CERTIFICATE OF CORRECTION

PATENT NO. : 4,740,231
DATED : Apr. 26, 1988
INVENTOR(S) : Gehring et al.

It is certified that error appears in the above-identified patent and that said Letters Patent is hereby corrected as shown below:

| | |
|---|---|
| Col. 4, line 40 | Delete "," after --by-- |
| Col. 10, line 67 | Insert --+-- before "80" |
| Col. 11, line 43 | Correct spelling of --particularly-- |
| Col. 16, line 47 | Correct spelling of --fertilizers-- |
| Col. 17, line 9 | Insert -- - -- before "2" |
| Col. 22, line 10 | Delete "of" and substitute --a-- |
| Col. 22, line 18 | Correct spelling of --dioxopyrrolidinyl |
| Col. 24, line 17 | Insert --wherein-- after "$R^6$," |
| Col. 25, line 14 | Correct spelling of --dialkoxyalkyl-amino-pyrazole-- |
| Col. 26, line 1 | Delete "presents" and substitute --represents-- |

Signed and Sealed this

Twentieth Day of December, 1988

Attest:

DONALD J. QUIGG

*Attesting Officer*   *Commissioner of Patents and Trademarks*